United States Patent [19]
Stevenson

[11] Patent Number: 5,718,689
[45] Date of Patent: Feb. 17, 1998

[54] FREE-STANDING SAFETY CAP FOR PERMANENTLY STORING CONTAMINATED MEDICAL INSTRUMENTS

[76] Inventor: John A. Stevenson, 14835 Telegraph Rd., Santa Paula, Calif. 93060

[21] Appl. No.: 679,615

[22] Filed: Jul. 10, 1996

[51] Int. Cl.[6] .................................................. A61M 5/00
[52] U.S. Cl. .......................... 604/192; 604/263; 128/919; 206/365
[58] Field of Search .......................... 604/192, 187, 604/263, 110; 128/919; 206/365, 366

[56] References Cited

U.S. PATENT DOCUMENTS

| | | | |
|---|---|---|---|
| 3,559,645 | 2/1971 | Schaller | 128/216 |
| 4,240,427 | 12/1980 | Akhavi | 128/218 |
| 4,468,223 | 8/1984 | Minagawa | 604/199 |
| 4,610,667 | 9/1986 | Pedicano et al. | 604/192 |
| 4,735,617 | 4/1988 | Nelson et al. | 604/263 X |
| 4,846,811 | 7/1989 | Vanderhoof | 604/263 |
| 4,874,384 | 10/1989 | Nunez | 604/198 |
| 4,883,470 | 11/1989 | Haindl | 604/192 |
| 5,026,345 | 6/1991 | Teringo | 604/110 |
| 5,053,018 | 10/1991 | Talonn | 604/198 |
| 5,078,696 | 1/1992 | Nedbaluk | 604/192 |
| 5,176,633 | 1/1993 | Sit | 604/86 |
| 5,342,309 | 8/1994 | Hausser | 604/110 |
| 5,505,705 | 4/1996 | Galpin et al. | 604/192 |

FOREIGN PATENT DOCUMENTS

WO9206724  4/1992  Germany.

*Primary Examiner*—John D. Yasko
*Attorney, Agent, or Firm*—Koppel & Jacobs

[57] ABSTRACT

A free-standing safety cap for storing contaminated medical instruments includes a sleeve, a stand on one end of the sleeve and a one-way locking mechanism on the other end. A user places the cap on a flat surface so that it is free standing and, without grasping the cap, inserts the instrument's contaminated sharp end into the cap. The one-way locking mechanism permanently secures the contaminated sharp end inside the cap. The stand can be formed with an opening for accessing the sleeve so that the cap can used for storing both the sterile and the contaminated instrument. This greatly reduces the risk of accidental puncture wounds to the cleaning and waste disposal personnel.

16 Claims, 7 Drawing Sheets

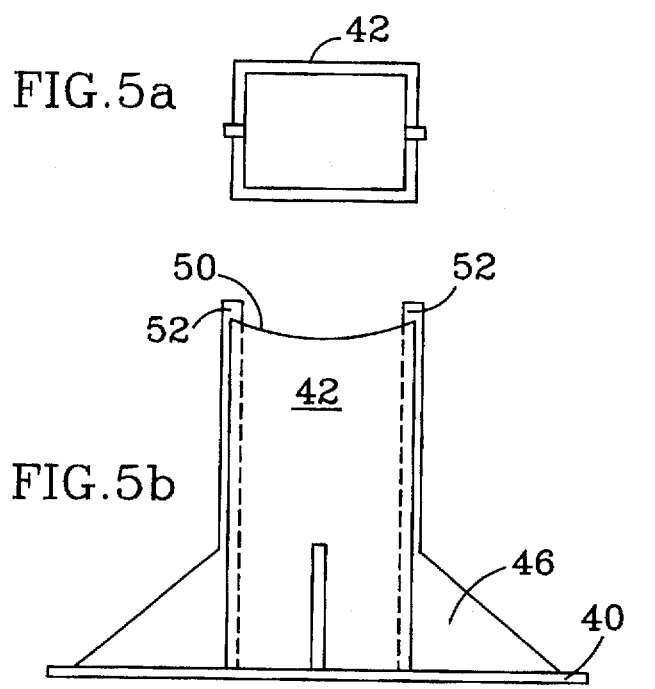
FIG.5a
FIG.5b
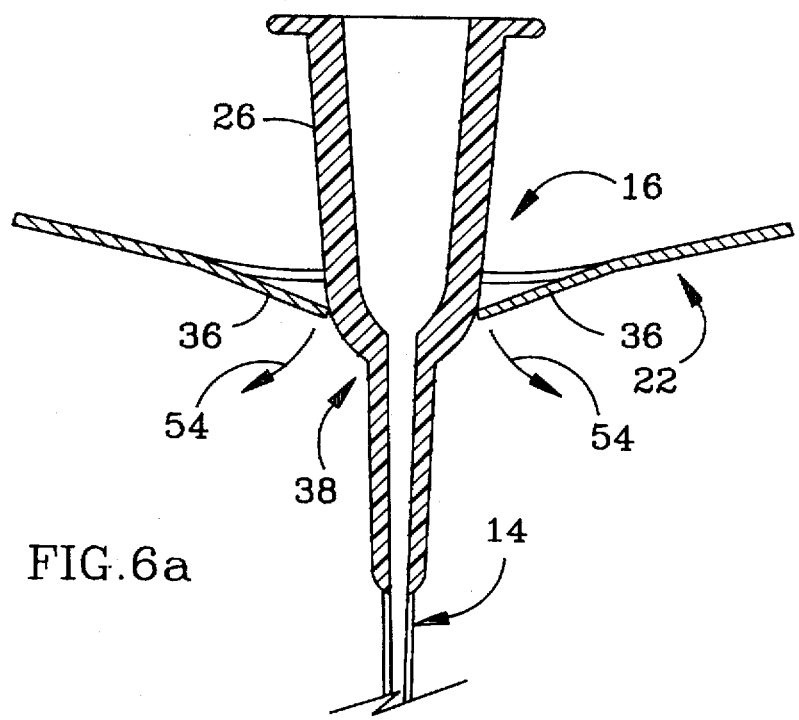
FIG.6a

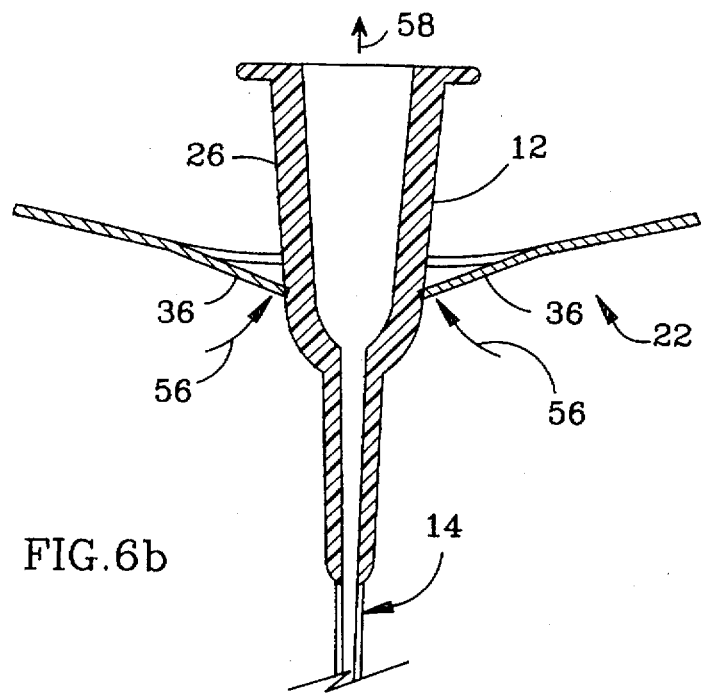
FIG.6b
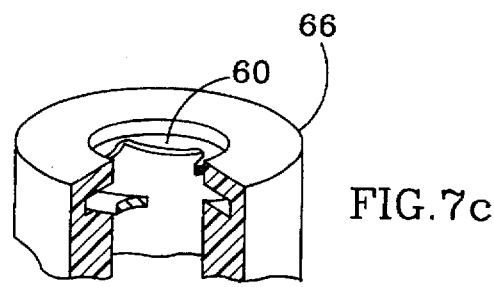
FIG.7c
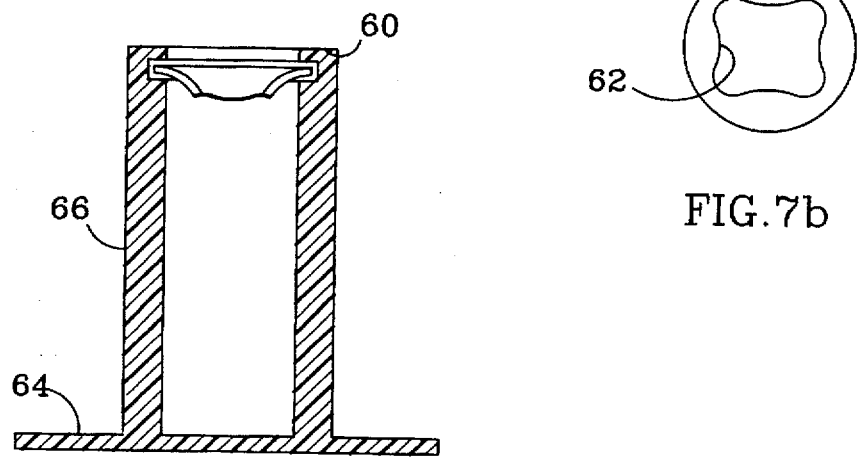
FIG.7a
FIG.7b

5,718,689

FREE-STANDING SAFETY CAP FOR PERMANENTLY STORING CONTAMINATED MEDICAL INSTRUMENTS

RELATED APPLICATION

This application is related to application Ser. No. 08/345 611 entitled "Safety Cap and Hub for Medical Instruments" filed Nov. 28, 1994 now U.S. Pat. No. 5,554,129 by the applicant of the present invention.

BACKGROUND OF THE INVENTION

1. Field of the Invention

The present invention generally relates to the storage and disposal of sharp medical instruments such as contaminated hypodermic needles, and more specifically to a safety cap for use with a complementary instrument hub such as a conventional needle hub or scalpel blade holder.

2. Description of the Related Art

Hypodermic needles are used to give injections and draw blood from patients. These needles can become contaminated with any number of infectious and potentially lethal diseases. Other medical instruments such as scalpels can become similarly contaminated. The threat of accidental puncture wounds from contaminated needles or scalpels poses a significant safety risk to medical personnel, hospital cleaning staff, waste disposal workers and the general public.

Until the early 1980's, it was standard practice to "recap" a needle after use. This required the user to grasp the narrow plastic sleeve in one hand, and with the other hand insert the contaminated needle into the sleeve. These sleeves were designed primarily to provide physical protection for the needle and to maintain sterility before use. Because of the sleeve's size and shape, a user could very easily miss the sleeve and puncture his or her hand. Furthermore, the cap could be accidentally or intentionally removed, thereby exposing the contaminated needle.

The medical community recognized this danger and adopted a policy against recapping. Instead, medical treatment areas are supposed to be equipped with special "sharps containers" for disposing contaminated sharp objects such as hypodermic needles or scalpels. These containers are typically fitted with either flexible plastic flaps or fixed baffles over their openings. The flaps are formed from a plastic diaphragm which has a hole at its center with slits extending radially outward from the hole. These designs are supposed to allow contaminated objects to be pushed through the opening, but prevent them from falling back out of the container. As a practical matter, sharps containers cannot be provided immediately adjacent every location where injections are being given, blood is being drawn or incisions are being made. Therefore, the user must carry the exposed contaminated needle or scalpel some distance before disposing of it. Furthermore, the sharp instruments have managed to back out of the container's opening or poke through its walls, posing a significant safety risk.

U.S. Pat. No. 4,883,470, "Safety Cap", discloses a flared cap for storing the needle and cannula hub before and after use. The cap and cannula hub have complementary rib designs which allow a syringe to both engage the hub and remove the needle from the cap prior to use, and to reinsert the contaminated needle into the cap and disengage the syringe. The flared cap reduces the risk of self-puncture, but the user must still grasp the cap with his off hand to recap the needle. Furthermore, the recapped contaminated needle can be withdrawn from the cap by reengaging a syringe.

U.S. Pat. No. 5,026,345, "Non-Mechanical Incapacitation Syringe Safety Needle Guard", discloses an enlarged flange for guiding a contaminated needle into a long narrow sheath to prevent the user from puncturing his hand during insertion. The insertion of the needle into the guard punctures a membrane thereby releasing an adhesive that permanently seals the contaminated needle inside the guard.

U.S. Pat. Nos. 4,846,811, 4,874,384, 5,342,309 and 5,053,018 disclose slidable or telescoping sleeves that fit over the syringe. The sleeves are retracted to expose the needle, and then slid down and locked to shield the tip. These syringes are awkward to use due to the extra bulk on the syringe itself. Furthermore, the incorporation of moveable parts increases the cost and reduces the reliability; moving parts break.

SUMMARY OF THE INVENTION

The present invention seeks to provide a simple and cost effective safety cap that will allow the user to permanently store a contaminated sharp instrument in the safety cap without having to grasp the cap to insert the used instrument.

This is accomplished with a free-standing safety cap with a sleeve for permanently securing the used sharp instrument, such as hypodermic needle or scalpel blade. The safety cap is designed to work with a needle which is mounted in a plastic hub, such as a standard conventional hypodermic needle, or with a needle which may be mounted directly in a syringe, such as, for example, a standard conventional insulin syringe with needle. In the case of a scalpel blade, the device is designed to work with a blade which is affixed in a disposable plastic handle. A stand supports the cap in a position in which an opening into the sleeve is exposed to receive the used sharp instrument. This opening is fitted with a one-way locking mechanism, which will allow the plastic hub, or base, syringe or handle to slide into the opening, and will lock onto the plastic part and securely prevent it from being pulled back out. The syringe can be optionally disengaged from the captured contaminated needle.

Three different alternative configurations are envisioned for the safety cap. In the simplest configuration, the cap has a single sleeve and a single opening into that sleeve, for receiving the contaminated sharp instrument. In practical use, this type of safety cap would typically be supplied separate from the needle or other sharp instrument which it is designed to contain. Safety caps of this type could be supplied non-sterile, in bulk packaging, for use at the treatment site to quickly and easily contain the contaminated sharp instrument and render it harmless to the user or others.

In a second configuration, the safety cap may be supplied with a second sleeve, also having a single opening but without a locking mechanism; this sleeve is intended to contain the sterile instrument prior to use. In practical application, this type of safety cap would be supplied together with the sterile sharp instrument in a single package, with the needle or other sharp instrument stored within the second sleeve prior to use.

In the third configuration, the safety cap has only a single sleeve which is intended to contain the sharp instrument both before and after use. As described above, the sleeve has an opening with a locking mechanism for securely containing the used sharp instrument. In addition, the same sleeve has a second opening which does not have a locking mechanism, and typically opens into the opposite end of the sleeve from the locking opening. In practical application, this type of safety cap would also be supplied together with the needle or other sharp instrument in a single package.

Prior to use, the sterile needle would be supplied with the needle inserted into the non-locking opening for storage of the needle with the sleeve prior to use. The length of the sleeve is such that the sharp object is sufficiently recessed below the unused opening in the opposite end, to prevent contact with a finger or any other body part of the user. After use, the contaminated sharp instrument is inserted and locked into the locking end of the same sleeve. Again, the length of the sleeve provides sufficient recess of the sharp object below the opening in the opposite end, to prevent human contact. As compared to the safety cap configuration which has two sleeves, this third configuration has the advantage of smaller size, but has the disadvantage that the tip of the used sharp instrument is not completely enclosed within the sleeve, but is protected by it's recessed position.

For a better understanding of the invention, and to show how the same may be carried into effect, reference will now be made, by way of example, to the accompanying drawings.

BRIEF DESCRIPTION OF THE DRAWINGS

FIGS. 5a and 5b are a view along section B—B and a perspective view, respectively, of the plastic base shown in FIG. 1.

FIGS. 6a and 6b are sectional views illustrating the function of the spring-metal clip to grip the conventional needle hub and prevent removal from the safety-cap during and after insertion, respectively.

FIGS. 7a through 7c are respectively sectional, plan, and partially cut-away perspective views of an alternate embodiment of the safety-cap.

DETAILED DESCRIPTION OF THE INVENTION

The invention provides a free-standing safety cap design for use with a conventional instrument hub or handle that reduces the risk of accidental puncture wounds for contaminated sharp medical instruments such as hypodermic needles and scalpels. The user places the cap on a flat surface so that it is free standing and inserts the contaminated instrument without grasping the cap. The cap allows the user to permanently secure the contaminated instrument without having to grasp the cap in his or her off hand until after the contaminated instrument is safely captured inside the cap. Furthermore, the cap provides a one-way locking mechanism that permanently secures the sharp end of the contaminated instrument inside the cap. This greatly reduces the risk of accidental puncture wounds to the cleaning and waste disposal personnel. The safety cap is described with respect to the standard hypodermic needle and plastic needle hub that are currently used in the medical profession, but is applicable to other types of sharp medical instruments.

Figure 1:
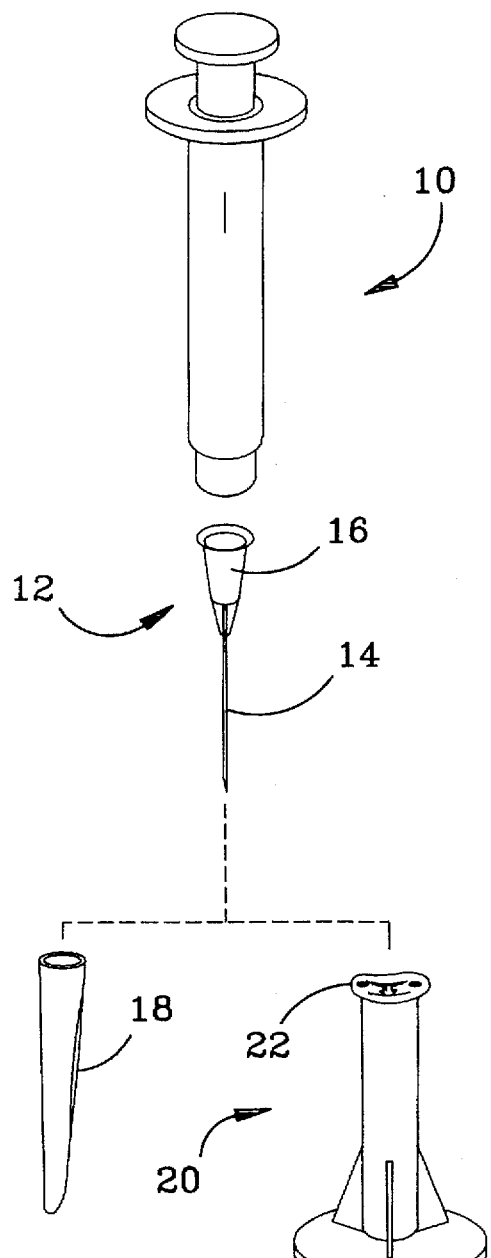
FIG. 1 is a partially exploded view of a standard hypodermic syringe, needle-hub assembly, and needle cap for capping the sterile needle, and in accordance with the present invention, a free-standing safety cap for permanently securing the contaminated needle.

FIG. 1 is a partially exploded view of a syringe 10 and a hypodermic needle-hub assembly 12 including a needle 14 attached to a hub 16. A conventional needle cap 18 is used to protect the sterile needle 14. After use, a free-standing safety cap 20 captures and permanently secures the contaminated needle 14. A one-way locking mechanism such as a spring clip 22 locks the needle hub 16 in place thereby preventing the contaminated needle 14 from being pulled back out of the safety cap 20.

The hypodermic syringe 10 and the needle-hub assembly 12 are preferably supplied in sterile packages, either separately, or assembled together as a single unit. The sterile needle is preferably supplied with a disposable conventional needle cap 18 which is not intended to be used for recapping the needle because of risk of self-puncture. The free-standing safety cap 20 may either be supplied together with the needle-hub assembly in the same sterile package, or it may be supplied separately in which case it need not be sterile.

To give an injection or draw blood, the user removes the sterile syringe 10 and needle 14 from the sterile package and attaches the syringe to the needle-hub assembly 12, with the sterile conventional needle cap 18 still covering the needle 14. The safety cap 20 is placed on a flat surface, such as a counter top or bedside table, adjacent to the treatment site. The bottom of the safety cap 20 may be coated with adhesive to help prevent tipping. Just prior to using the hypodermic assembly, the sterile conventional needle hub is removed and may be discarded.

Once the needle has been contaminated, the user, holding the syringe, inserts the used needle into an opening in the spring clip 22 at the upper end of the safety cap 20, and pushes the needle down into the cap until the plastic needle hub 16 engages into the jaws of the spring clip 22. The user's free hand is kept clear, and some distance away, during this procedure. The cap 20 with needle enclosed inside may then be disposed of, either with or without the syringe attached.

Figure 2:
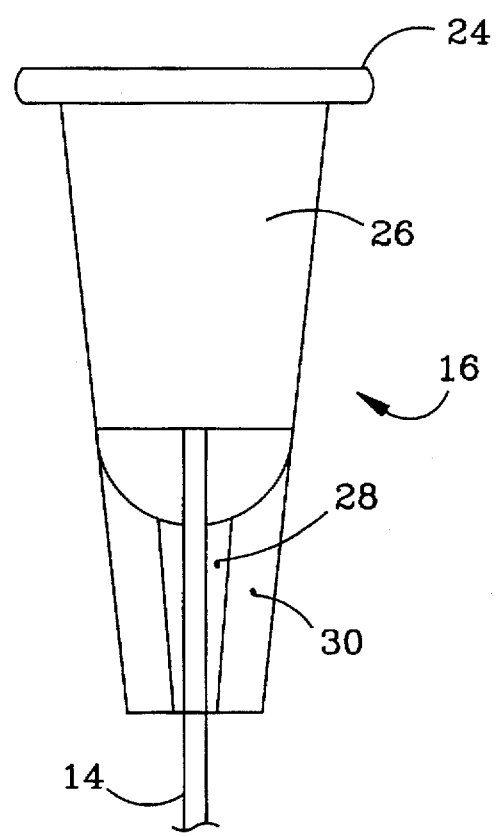
FIG. 2 is a side view of a known Luer-Lock needle hub commonly used in the medical industry that is compatible with the safety cap's locking mechanism.

As shown in FIG. 2, the standard Luer-Lock hub 16 of the type manufactured by Becton-Dickinson includes a flange 24, which is configured to thread into a threaded female Luer-Lock connector such as found on a syringe. A tapered section 26 with an internal hollow tapered cylinder designed to press fit over the nipple part of a female Luer-Lock connector is affixed to the flange 24. A smaller diameter cylindrical section 28 extends from the tapered section 26 with projecting vanes 30 which may engage complementary vanes or projections inside the needle cap to prevent the needle-hub assembly from rotating within the cap 18 shown in FIG. 1, and thereby facilitate connection of the needle-hub assembly to a syringe or other Luer-Lock device.

Figure 3:
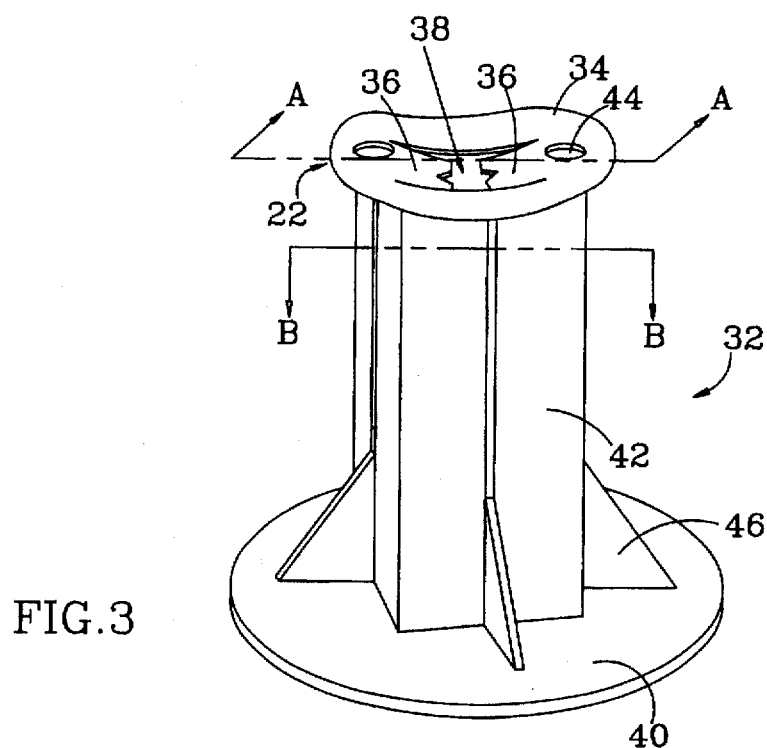
FIG. 3 is a perspective view of the Safety-Cap shown in FIG. 1.

As shown in FIG. 3, the safety cap 20 includes a plastic or polymer bottom section 32 and the spring metal clip 22.

The spring metal clip is comprised of a curved oval outer section 34, which supports a plurality of downward projecting teeth 36. The teeth form an opening 38 for receiving the needle hub, and the teeth are designed to allow easy insertion of the needle hub but to prevent it from being pulled back out. The plastic bottom section 32 includes a flat base 40, of sufficient size to allow the safety cap 20 to rest stably on a flat surface, and to prevent the safety cap from tipping when a needle and hub are inserted into the metal clip. The bottom of the base 40 may be coated with adhesive to improve stability.

A plastic or polymer sleeve 42 is affixed to the flat base 40 to receive and permanently contain the used needle or other sharp instrument. The sleeve 42 must be wide enough and tall enough to store the contaminated needle or instrument for which it is specifically designed. Typically the sleeve 42 is much taller than it is wide. For example, a sleeve for a standard hypodermic may be approximately 4 cm tall and 1.3 cm wide. As a result, unless the sleeve is made unnecessarily wide, it could not rest stably on the flat surface without the base 40.

A fastening mechanism 44 is provided at the other end of the sleeve 42 to securely fasten the spring metal clip 22 to the sleeve. As illustrated here, the fastening mechanism 44 consists of two plastic tabs which project upward through holes in the spring metal clip 22, and which are fused downward at the time of manufacture. A variety of alternative fastening mechanisms could be used. The sleeve 42 can have many different cross-sectional shapes; it may be polygonal, round, or oval, or any of a number of other shapes. Reinforcing struts 46 may be provided to strengthen the unit and provide added rigidity to the flat base.

Figure 4A:
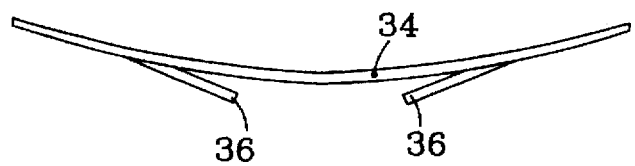
FIGS. 4a and 4b are a view along section A—A and a plan view, respectively, of the spring-metal clip shown in FIG. 1
Figure 4B:
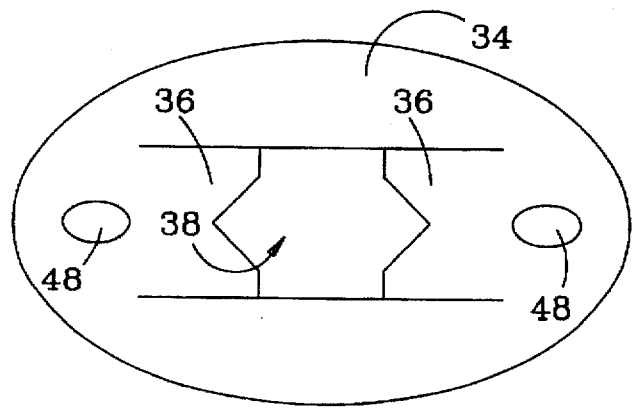

As shown in FIGS. 4a and 4b, the spring clip 22 is preferably formed of spring steel or another resilient metal which will tend to return to it's original shape when it has been deformed. As shown here, the metal clip comprises an oval outer section 34, which has a gentle downward curvature, and two downward projecting metal teeth 36. The space between the downward projecting teeth forms an opening 38 into which the needle hub may be inserted, and locked. The spring metal clip is also perforated by two holes 48 which are used to firmly secure the clip to the plastic bottom piece of the safety cap. This is accomplished with two complementary plastic or polymer tabs which project up from the bottom piece of the safety cap, and are melted or sonically fused at the time of manufacture to form a knob of plastic above the holes in the metal clip, of diameter greater than the holes, to effectively prevent the metal clip from separating from the plastic bottom piece. This design represents only one possible fastening mechanism; it is envisioned that a variety of different fastening mechanisms could be used.

As shown in FIGS. 5a and 5b, the plastic or polymer bottom piece 32 of the safety cap 20 includes the sleeve 42 that is affixed to the flat base 40 and projects upward and is open at the top. The upper end 50 of the sleeve is designed with a complementary shape to the curved spring metal clip and is provided with two upward projecting plastic tabs 52 which fit through complementary holes in the spring metal clip. Following assembly of the metal clip onto the bottom piece, these plastic tabs are melted or sonically fused to secure the metal clip to bottom piece and prevent it from being pulled off. Vanes 46 may be provided to strengthen the structure.

FIG. 6a is a cross sectional view of the plastic needle hub assembly 12 as it is pushed down into the spring metal clip 22. The needle hub is inserted into the opening 38 formed between the metal teeth 36. As the tapered upper part 26 of the needle hub is forced downward, the metal teeth 36 of the spring metal clip are bent progressively downward and farther apart, in the direction shown by arrow 54.

FIG. 6b shows a cross sectional view of the plastic needle hub 12 after it has been pushed sufficiently far into the metal clip 22 to become engaged within the clip. The spring metal teeth 36, attempting to return to their original conformation due to the resilience of the spring steel, will resist the downward and outward pressure from the needle hub, and will exert a counter pressure on the hub in an upward and squeezing direction, shown by arrow 56. This will cause the metal teeth 36 to form an indentation in the deformable plastic of the needle hub and they will engage the hub, preventing it from sliding back out from the opening between the teeth. If an effort is made to pull the needle hub back out from between the spring metal teeth by pulling upward on the needle hub in the direction illustrated by arrow 58, the metal teeth 36 are drawn closer together, in the direction shown by arrow 56, thus engaging the needle hub more firmly, and preventing it from being pulled back out.

An alternate embodiment of the safety cap's spring clip is shown in FIG. 7. This design uses a smaller spring metal clip 60 which is annular in shape, with four downward projecting metal teeth 62. The metal teeth 62 function in the same way to engage the plastic needle hub, as the metal teeth 36 function in the metal clip design illustrated in FIGS. 4a and 4b. The safety cap comprises a plastic or polymer base 64 of essentially the same cross-sectional shape as the base shown in FIG. 3, with the spring metal clip 60 being molded into the sleeve 66 at the time of manufacture. This safety cap design also differs from the design shown in FIGS. 5a and 5b, in that the sleeve 66 is this design preferably has a circular cross-section.

Figure 8A:
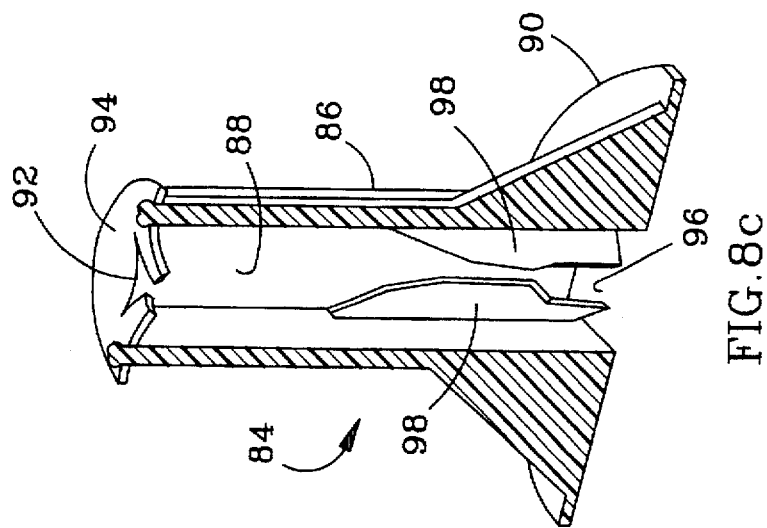
FIGS. 8a through 8c are sectional perspective views of three alternate embodiments of the safety-cap for securing the contaminated needle in a single sleeve, securing the sterile and contaminated needle in a pair of adjacent chambers, and securing the sterile and contaminated needle in the same single chamber, respectively.
Figure 8B:
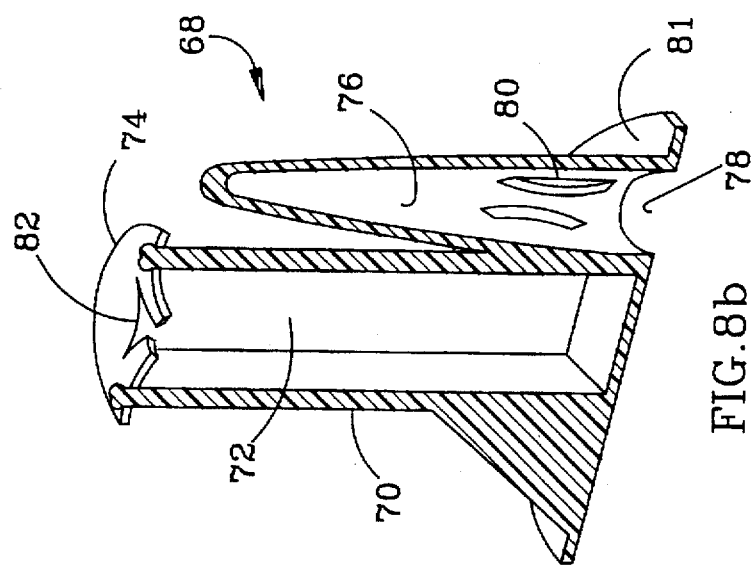
Figure 8C:
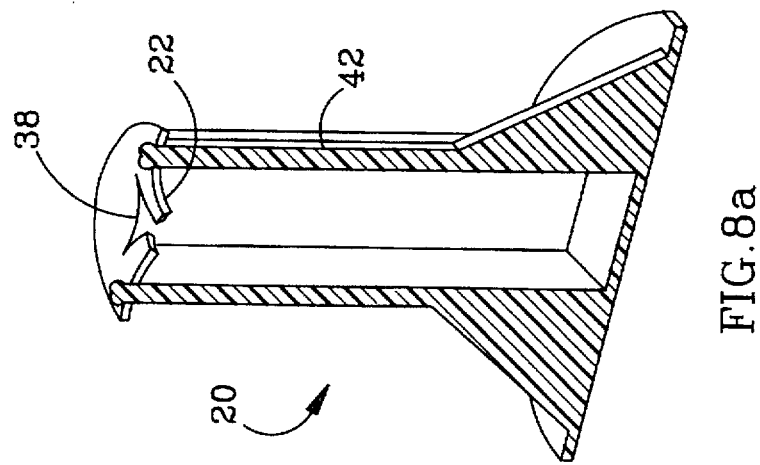

FIGS. 8a, 8b and 8c show three alternative configurations for the safety cap with respect to the arrangement of an opening for containing the needle or sharp instrument after use, and, in the case of FIGS. 8b and 8c, an additional opening for securing and protecting the sterile needle prior to use.

FIG. 8a shows a cut-away perspective view of the safety cap design 20 that was illustrated in FIGS. 1 through 5. This safety cap design has a single sleeve 42 for containing a used needle, and a single opening 38 which is supplied with a locking mechanism 22 for receiving the needle hub and preventing it from being pulled back out of the sleeve.

FIG. 8b shows a cut-away perspective view of an alternate embodiment of a safety cap 68. This safety cap comprises a plastic or polymer bottom piece 70 that is molded to define a sleeve 72 for receiving the used contaminated sharp instrument. The sleeve 72 is equipped with a metal clip 74 for securing the used needle hub and preventing it from being pulled back out. The bottom piece 70 is molded to define an additional sleeve 76 with an opening 78, which preferably opens into the base 80 of the safety cap, for the purpose of securing and protecting the sterile needle and hub prior to use.

The inner shape of the sleeve 76 is essentially the same as that of a conventional needle cap that is currently manufactured and supplied with a typical needle-hub assembly. The inner surface of sleeve 76 is formed with a plurality of inward-projecting ridges 80 which serve the purpose of engaging the vanes 30 of the conventional needle hub (shown in FIG. 2) to prevent rotation of the hub within the sleeve and allow the user to firmly secure the needle hub to a syringe by screwing it into the female Luer-lock connector on the end of the syringe.

The safety cap design shown in 8b replaces the function of both the conventional cap 18 and the safety cap 20 as shown in FIG. 1. The safety cap 68 will be provided in a sterile package from the manufacturer with the needle-hub assembly inserted into sleeve 76 via opening 78. The sterile package may also contain, optionally, a sterile syringe attached to the needle hub. To give an injection or draw blood, the user breaks the sterile seal, removes the needle and cap assembly and attaches the needle hub to a syringe if not already supplied with syringe attached. The user then removes the needle from the safety cap for use, and places the safety cap on a stable flat surface adjacent to the treatment site. The safety cap is placed with the flat base 81 down and the opening 82 to sleeve 72 pointing upward with the metal clip 74 exposed.

Once the needle has been contaminated, and with his other hand held at a distance away from the safety cap, the user inserts the used needle through the opening in the metal clip 74 into the sleeve 72 and pushes the needle down until the hub is engaged into the metal clip. The safety cap with needle and hub is then disposed of as a unit, either with, or without the syringe attached.

FIG. 8c shows a cut-away perspective view of another embodiment of a free-standing safety cap 84. This safety cap design comprises a plastic or polymer bottom piece 86 that is molded to form a sleeve 88 that is affixed to a flat base 90. The sleeve 88 has an opening 92 opposite the flat base 90 that is surmounted by a metal clip 94. The sleeve 88 has an opening 96 in the base 90 and is provided with inwardly projecting ridges or vanes 98 towards that end. These vanes are positioned and shaped so as to provide a snug fit to a conventional syringe hub such as shown in FIG. 2, and also to interlock with the vanes 30 on the syringe hub to prevent it from rotating within the sleeve. The metal clip 94 is designed to allow the easy insertion of needle and hub and to engage the plastic hub to prevent it from being pulled back out.

The safety cap 84 shown in FIG. 8c is used in the same manner as the safety cap 68 shown in FIG. 8b. The design shown in 8c differs from that shown in 8b, in that only one sleeve is used in 8c, to contain the sterile needle before use, and to contain the contaminated needle after use. This is accomplished through the provision of two separate openings into the sleeve 88. The top opening 92, opposite the base 90, is provided with a mechanism 94 to prevent the contaminated needle from being pulled back out, while the opening 96 which opens through the base 90, is fitted with a mechanism 98 to prevent the needle hub from rotating axially in the sleeve, and allows the needle and hub to be withdrawn and reinserted at will. The bottom piece of the safety cap is designed to provide a sleeve 88 of sufficient length that the tip of the needle, when inserted into either end of the sleeve, will be sufficiently recessed back from the opening in the opposite end of the sleeve to prevent contact with a finger or any other body part of the user or any other person who may come into contact with the safety cap, such as waste disposal personnel, housekeeping personnel, etc.

Figure 10A:
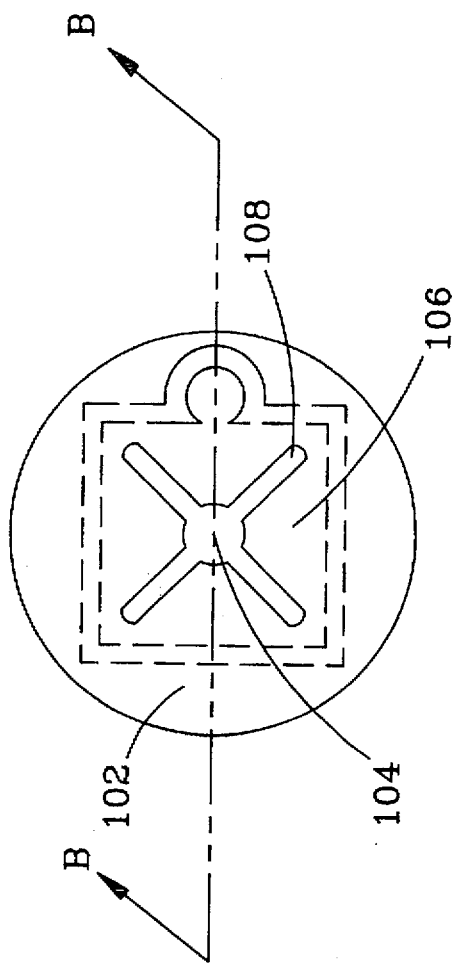
FIGS. 10a and 10b show a top view and a sectional view along section B—B of the plastic or polymer clip.
Figure 10B:
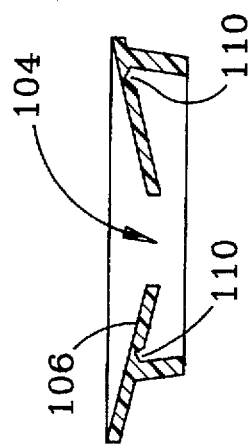
Figure 9:
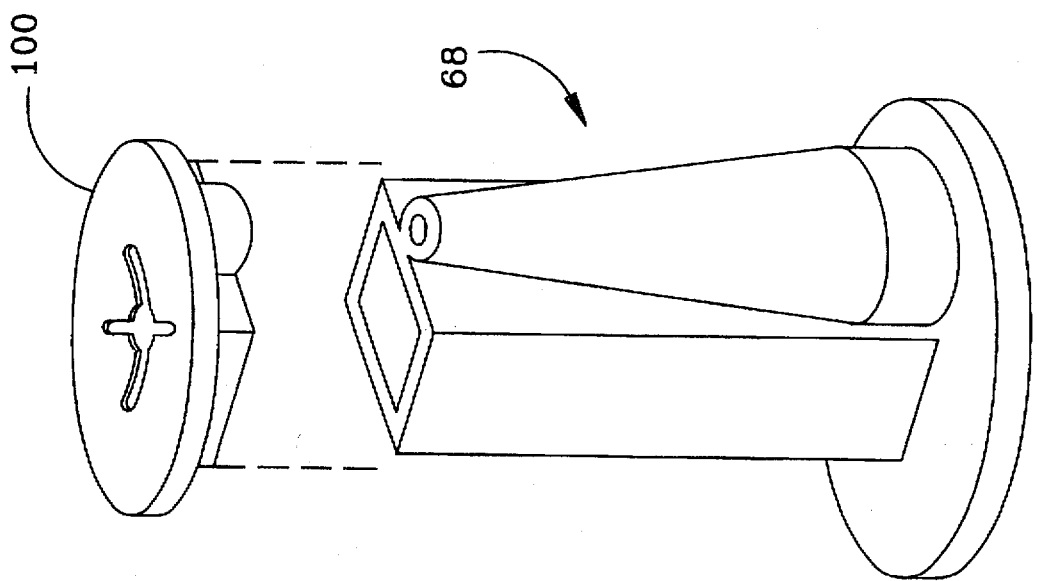
FIG. 9 shows a perspective view of the safety cap with an alternate plastic or polymer clip.

The safety cap designs shown in 8a, 8b and 8c may also be modified by replacing the spring metal clip with a plastic clip 100 as shown in FIGS. 9, 10a and 10b. The plastic clip comprises a funnel shaped rim 102 with a flexible center opening 104. The flexible opening 104 is provided with a plurality of flexible flanges 106. The flanges are made by forming radial slots 108 in the rim that are spaced around the opening 104 and extend outward from the opening. The flexibility of the flanges is increased by forming linear notches 110 in the underside of the plastic clip. The plastic clip 100 is designed to work not with a conventional needle hub such as shown in FIG. 2, but with a locking needle hub assembly shown in FIGS. 11 and 12.

Figure 11B:
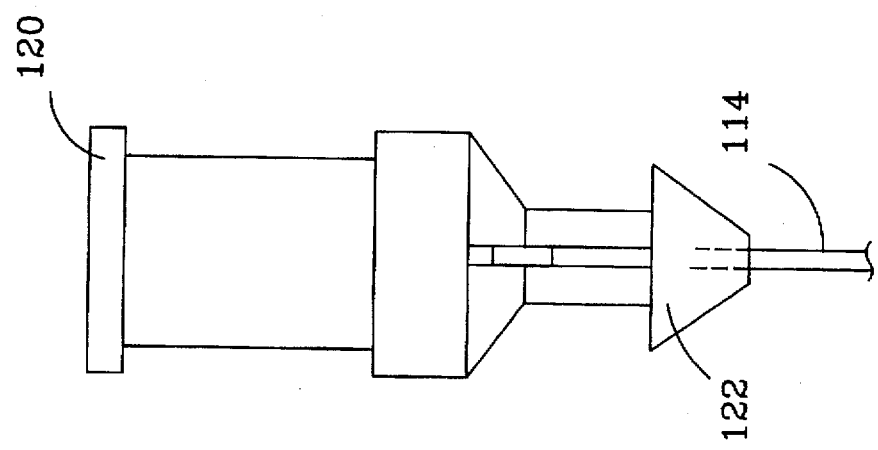
FIGS. 11a and 11b shows sectional and side views of the locking needle hub.
Figure 11A:
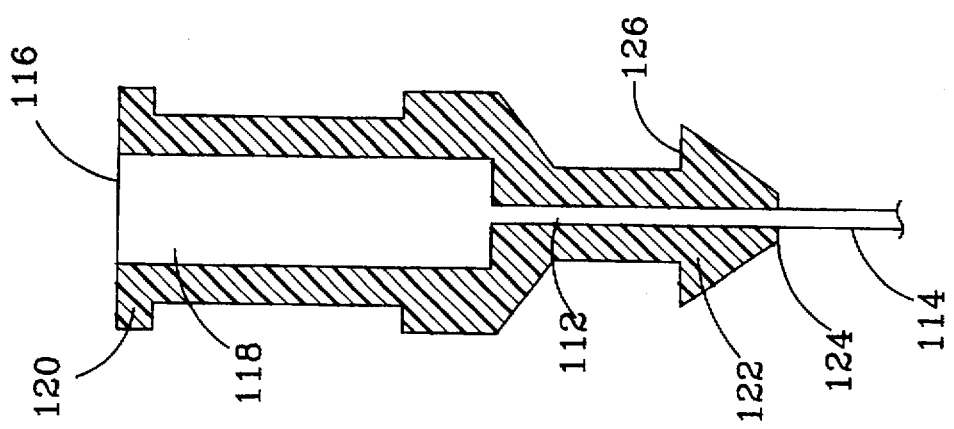

As shown in FIGS. 11a and 11b, the locking needle hub preferably comprises a hollow shaft 112 that is attached to needle 114. The opposite end 116 of the shaft is formed with an internal taper 118. The end 116 is provided with a Luer-lock flange 120 for connection to a conventional Leur-lock fitting on a syringe. The one-way locking mechanism is preferably a tapered stop 122 formed around the shaft 112. The stop's narrow end 124 faces the needle 114 and its base 126 faces the end 116 of the shaft. The ridge formed by the base is capable of engaging the plastic flanges 106 when the hub is inserted into the plastic clip 100 shown in FIGS. 10a and 10b, thereby preventing the hub and needle from being pulled back out of the clip.

Figure 12:
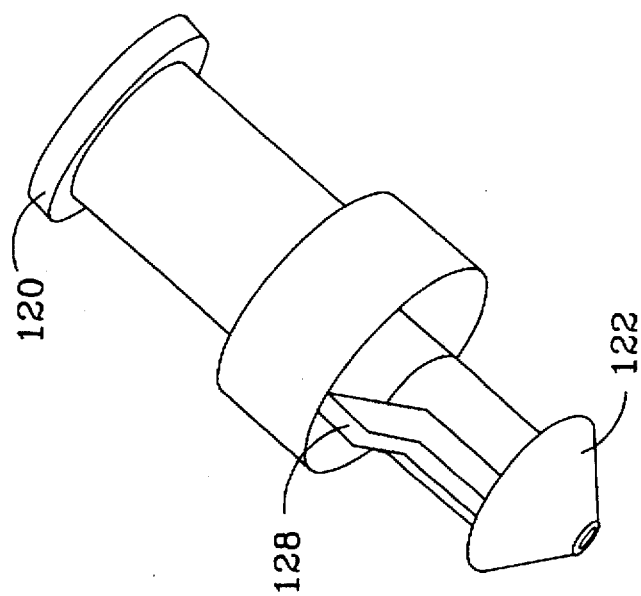
FIG. 12 shows a perspective view of the locking needle hub.

As shown in the perspective view of the locking needle hub, FIG. 12, the needle hub is also provided with a plurality of plastic wings 128, preferably 2. These wings perform substantially the same function as the vanes 36 on a conventional needle hub as shown in FIG. 2, to engage with complementary ridges within the needle cap to prevent the needle hub assembly from rotating within the cap. In addition, these wings can engage with the slots 108 in the plastic or polymer clip assembly shown in FIGS. 10a and 10b, to prevent the used needle hub from turning within the safety cap and thus allow disengagement of the syringe from the used needle hub.

The bottom piece design shown in FIG. 8c, having a single sleeve with two openings, when provided with a plastic or polymer clip similar to 100 in FIGS. 9 and 10, results in a design in which the clip and bottom piece may all be molded together in a single injection mold. This will reduce the production cost of the unit by eliminating the need to mold the bottom piece and the clip separately and then fuse them together.

The described safety cap designs reduce the risk of accidental puncture wounds. The free-standing safety cap receives the contaminated needle or scalpel without requiring the user to hold onto the cap, and thus reduces the risk of self-puncture wounds. Once the needle or blade is reinserted, it is permanently secured inside the cap; this reduces the risk to personnel charged with disposing of the contaminated instruments.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

I claim:

1. A free-standing safety cap, comprising
   a sleeve with upper and lower ends and having an opening formed in its upper end;
   a stand that is affixed to the sleeve's lower end for supporting the sleeve in a position in which the opening is exposed so that an instrument having a hub and a contaminated sharp end can be inserted into the sleeve without grasping the cap during insertion; and
   a one-way locking mechanism for engaging the instrument's hub to permanently secure the contaminated sharp end of the instrument inside the sleeve, said one-way locking mechanism comprising:

an annular member on said sleeve at its upper end that defines the opening in the sleeve; and a plurality of metal teeth spaced around an interior edge of the annular member that project inward and towards the lower end of the sleeve, said metal teeth resisting the downward and outward pressure from the instrument's hub during insertion such that the metal teeth engage the hub and inhibit it from being withdrawn from the cap.

2. The free-standing safety cap of claim 1, wherein said annular member is a discrete annular metal member that is affixed to the sleeve at its upper end.

3. A free-standing safety cap, comprising:

a sleeve with upper and lower ends and having openings formed in its upper and lower ends;

a stand that is affixed to the sleeve's lower end for supporting the sleeve in a position in which the opening in its upper end is exposed so that an instrument having a hub and a contaminated sharp end can be inserted into the sleeve without grasping the cap during insertion; and a one-way locking mechanism for engaging the instrument's hub to permanently secure the contaminated sharp end of the instrument inside the sleeve, said stand comprising an annular base that extends laterally from the sleeve at its lower end so that the instrument's sharp end can be secured inside the sleeve before use and withdrawn from the sleeve through the opening in its lower end.

4. The free-standing safety cap of claim 3, further comprising:

a sterile hypodermic assembly in said sleeve, said hypodermic assembly having a hub and a sterile needle; and a locking mechanism inside the sleeve towards its lower end that is shaped to provide a snug fit with the assembly's hub so that the sterile needle is recessed from the opening in the sleeve's upper end and to prevent rotation of the sterile hypodermic assembly so that a syringe can be engaged to the hub to remove the sterile needle from the sleeve.

5. The free-standing safety cap of claim 4, wherein said one-way locking mechanism comprises:

a annular member on said sleeve at its upper end that defines its opening; and a plurality of metal teeth spaced around an interior edge of the annular member that project into and towards the lower end of the sleeve, said metal teeth resisting the downward and outward pressure from the instrument's hub during insertion such that the metal teeth engage the hub and inhibit it from being withdrawn from the cap so that the contaminated needle is recessed from the opening in the sleeve's lower end.

6. A free-standing safety cap, comprising:

a sleeve having upper and lower ends with respective openings;

a sterile instrument in said sleeve, said instrument having a hub and a sterile sharp end;

a locking mechanism inside the sleeve towards its lower end that is shaped to provide a snug fit with the instrument's hub so that its sterile sharp end is recessed from the opening in the sleeve's upper end;

a stand that is affixed to the sleeve's lower end for supporting the sleeve in a position in which the opening in the sleeve's upper end is exposed so that a used instrument's contaminated sharp end can be inserted into the sleeve without grasping the cap during insertion; and a one-way locking mechanism at the upper end of the sleeve for engaging the instrument's hub to permanently secure its contaminated sharp end inside the sleeve and recessed from the opening in the sleeve's lower end.

7. The free-standing safety cap of claim 6, wherein said one-way locking mechanism comprises:

a annular member on said sleeve at its upper end that defines that opening; and a plurality of metal teeth spaced around an interior edge of the annular member that project inward and towards the lower end of the sleeve, said metal teeth resisting the downward and outward pressure from the instrument's hub during insertion such that the metal teeth engage the hub and inhibit it from being withdrawn from the cap.

8. The free-standing safety cap of claim 6, wherein said one-way locking mechanism comprises:

a flexible annular member on said sleeve at its upper end that defines its opening, said flexible annular member having a plurality of flexible flanges that are deflectable to receive and then secure said hub.

9. The free-standing safety cap of claim 6, wherein said stand comprises:

an annular base that extends laterally from the sleeve at its lower end so that the instrument's sharp end can be secured inside the sleeve before use and withdrawn from the sleeve through the opening in its lower end.

10. The free-standing safety cap of claim 6, wherein the instrument comprises a hypodermic assembly, said locking mechanism inside the sleeve preventing rotation of the hypodermic assembly so that a syringe can be engaged to the hub to remove the sterile needle from the sleeve.

11. A method for capping a contaminated medical instrument, comprising:

providing a free-standing safety cap having a sleeve with upper and lower ends with an opening formed in its upper end, a stand that is affixed to the sleeve's lower end, and a one-way locking mechanism at the sleeve's upper end;

placing the safety cap's stand on a surface so that the safety cap is supported in a position at which the opening to the sleeve is exposed to receive a sharp end of a medical instrument; and without grasping the safety cap, inserting the instrument's sharp end through the opening so that the one-way locking mechanism engages the medical instrument to permanently secure its contaminated sharp end in the sleeve, said one-way locking mechanism comprising a plurality of teeth spaced around the opening in the sleeve that project inward and towards the lower end of the sleeve, said teeth resisting the downward and outward pressure from the instrument's hub during insertion such that the teeth engage the hub and inhibit it from being withdrawn from the cap.

12. The method of claim 11, wherein said medical instrument comprises a syringe coupled to a hypodermic assembly that includes a hub and a needle, said teeth inhibiting rotation of said hypodermic assembly, further comprising:

grasping the safety cap in one hand while turning said syringe with the other hand to disengage the syringe from said hypodermic assembly; and withdrawing said syringe from the safety cap.

13. A method for capping a contaminated medical instrument, comprising:

providing a free-standing safety cap comprising a sleeve having upper and lower ends with respective openings, a sterile medical instrument in said sleeve, said medical instrument having a hub and a sterile sharp end, a locking mechanism inside the sleeve towards its lower end that is shaped to provide a snug fit with the instrument's hub so that its sterile sharp end is recessed from the opening in the sleeve's upper end, a stand that is affixed to the sleeve's lower end, and a one-way locking mechanism at the sleeve's upper end;

a user grasping said safety cap in one hand while withdrawing the medical instrument from the sleeve through the opening in its lower end with the user's other hand;

using the medical instrument to perform a medical procedure;

placing the safety cap's stand on a surface so that the safety cap is supported in a position at which the opening in the sleeve's upper end is exposed to receive the contaminated sharp end of the medical instrument; and without grasping the safety cap, inserting the medical instrument's sharp end through the opening in the sleeve's upper end so that the one-way locking mechanism engages the medical instrument to permanently secure its contaminated sharp end in the sleeve and recessed from the opening in its lower end.

14. The method of claim 13, wherein said medical instrument is a hypodermic assembly that includes a needle and said hub, and said instrument is withdrawn by:

attaching a syringe to said hub; and pulling said syringe to withdraw the hypodermic assembly.

15. The method of claim 14, wherein said one-way locking mechanism inhibits rotation of said hypodermic assembly, further comprising:

grasping the safety cap in one hand while turning said syringe with the other hand to disengage the syringe from said hypodermic assembly; and withdrawing said syringe from the safety cap.

16. The method of claim 13, wherein the one-way locking mechanism comprises a plurality of teeth spaced around the opening in the sleeve that project inward and towards the lower end of the sleeve, said teeth resisting the downward and outward pressure from the instrument's hub during insertion such that the metal teeth engage the hub and inhibit it from being withdrawn from the cap.

* * * * *